United States Patent [19]
Zeitvogel et al.

[11] Patent Number: 5,145,791
[45] Date of Patent: Sep. 8, 1992

[54] 3-METHOXY-4-HYDROXYPHENYLGLYCOL FLUORESCENCE POLARIZATION IMMUNOASSAY

[75] Inventors: Christine H. Zeitvogel, Wildwood; Maciej B. Adamczyk, Lindenhurst; David A. Betebenner, Vernon Hills, all of Ill.; Kenward S. Vaughan, Carlsbad, Calif.

[73] Assignee: Abbott Laboratories, Abbott Park, Ill.

[21] Appl. No.: 768,096

[22] Filed: Sep. 30, 1991

Related U.S. Application Data

[63] Continuation of Ser. No. 554,111, Jul. 18, 1990, abandoned, which is a continuation of Ser. No. 346,509, May 2, 1989, abandoned, which is a continuation of Ser. No. 883,898, Jul. 9, 1986, abandoned.

[51] Int. Cl.$^5$ ............... G01N 33/533; A61K 39/385; A61K 39/395
[52] U.S. Cl. ..................... 436/546; 435/7.1; 436/447; 436/547; 436/548; 530/363; 530/389.8; 530/389.2; 549/223; 549/225
[58] Field of Search ............... 436/527, 546, 547, 548, 436/172, 825, 822; 549/223, 225; 530/363, 807, 387; 435/7.1, 961

[56] References Cited
U.S. PATENT DOCUMENTS

| | | | |
|---|---|---|---|
| 4,420,568 | 12/1983 | Wang | 436/800 |
| 4,476,229 | 10/1984 | Fino | 549/223 |
| 4,510,251 | 4/1985 | Kirkemo | 549/223 |
| 4,585,862 | 4/1986 | Wang | 549/225 |

OTHER PUBLICATIONS
Keeton: Science 211, pp. 586–588, (1981).

*Primary Examiner*—Esther L. Kepplinger
*Assistant Examiner*—Lora M. Green
*Attorney, Agent, or Firm*—Thomas M. Breininger

[57] ABSTRACT

The present invention is directed to a fluoroescence polarization immunoassay for determining the 3-methoxy-4-hydroxyphenylglycol content in body fluids, to the various components needed for preparing and carrying out such an assay, and to methods of making these components. Specifically, tracers, immunogens and antibodies are disclosed, as well as methods for preparing them. The assay is conducted by measuring the degree of polarization of plane polarized light that has been passed through a sample containing antiserum and tracer.

4 Claims, 5 Drawing Sheets

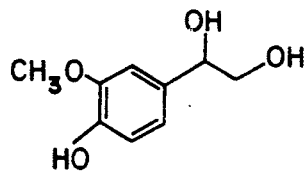
Fig. 1
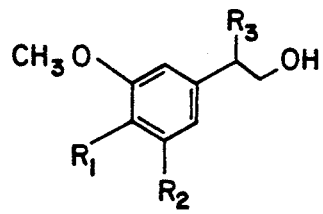
Fig. 2
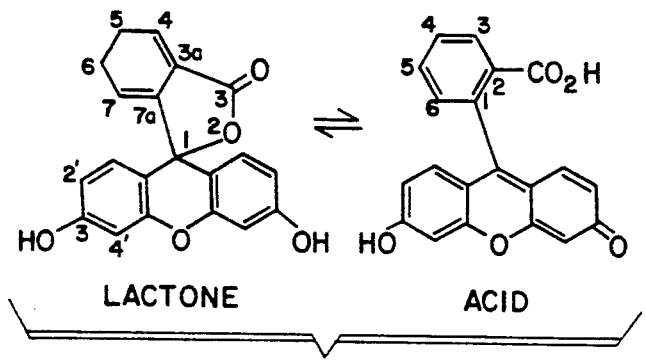
Fig. 3
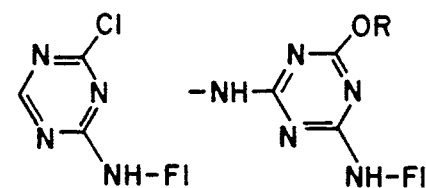
Fig. 4-1   Fig. 4-2
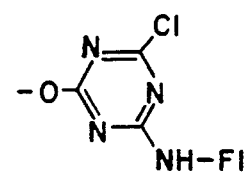
Fig. 4-3
-NH-CO-Fl   -CO-NH-Fl   -C(NH)-NH-Fl   -NH-CO-NH-Fl
Fig. 4-4   Fig. 4-5   Fig. 4-6   Fig. 4-7
-NH-CS-NH-Fl   -O-CO-NH-Fl   -O-CS-NH-Fl
Fig. 4-8   Fig. 4-9   Fig. 4-10
-SO$_2$-NH-Fl        -O-CO-NH-SO$_2$-NH-Fl
Fig. 4-11            Fig. 4-12

3-METHOXY-4-HYDROXYPHENYLGLYCOL FLUORESCENCE POLARIZATION IMMUNOASSAY

This application is a continuation of application Ser. No. 554,111, filed Jul. 18, 1990, now abandoned, which is a continuation of application Ser. No. 346,509, filed May 2, 1989, now abandoned, which is a continuation of application Ser. No. 883,898, filed Jul. 9, 1986, now abandoned.

BACKGROUND OF THE INVENTION

1. Technical Field

The present invention relates to a method and reagents for a fluorescence polarization immunoassay (FPIA) procedure for quantitating 3-methoxy-4-hydroxyphenylglycol (MHPG) levels in biological fluids such as urine, serum or plasma, which assay is characterized by the use of a novel stabilizing matrix for the fluorescent tracers used therein and by an improved specimen preparation method utilizing a magnesium silicate resin for reduction of specimen background and interfering metabolites.

2. Background Art

MHPG is the principal metabolite of the neurotransmitter norepinephrine in the central nervous system. Pretreatment MHPG levels in urine or blood provide the physician with information that aids in discriminating among subgroups of the major depressive disorders and that may aid in predicting patient response to specific antidepressants. Several studies have shown that differences in MHPG metabolism provide the basis for tentative identification of three biochemically discrete subgroups of the major depressive disorders. The first subgroup comprises bipolar manic depression, schizoaffective depression and some cases of unipolar endogenous depression. Patients in this subgroup excrete low levels of MHPG ($x<1.9$ mg/24 hour) and may have low norepinephrine output. Patients in the second subgroup, presenting symptoms of endogenous depression, excrete intermediate levels of MHPG (1.9 mg/24 hours$\leq x \leq$2.5 mg/24 hours) and may have normal norepinephrine metabolism with abnormalities in other neurochemical systems. The third subgroup includes patients with symptoms of unipolar endogenous depression. These patients are characterized by high MHPG levels ($x>2.5$ mg/24 hour), may have high norepinephrine output and, in the case of a somewhat discrete second tier subgroup, may also hypersecrete urinary cortisol.

First and second subgroup patients show a positive response to an amphetamine challenge, while third subgroup patients generally yield a negative response. Urinary and blood MHPG levels are predictive of the effectiveness of antidepressant drug therapy only for the unipolar endogenous depressive patients of the first subgroup. MHPG levels in the second and third subgroups have not been shown to have predictive value as to the success of drug treatment, and response to antidepressant therapy varies widely. Urinary and blood MHPG levels in patients with bipolar manic depression vary with alterations in affective state. Generally, these patients excrete lower levels of MHPG during depressive episodes, with higher MHPG levels during manic or hypomanic episodes than during periods of clinical remission.

Paper chromatography, spectrophotometric or fluorometric measurement, gas chromatography with flame ionization detection or electron capture detection, and radioimmunoassay have been described in the literature for MHPG determination in urine. Methods involving gas chromatography with mass spectrometry and high performance liquid chromatography with electrochemical or fluorescence detectors have also proven suitable for MHPG measurement.

In general, competitive binding immunoassays have provided a preferable alternative to chemical methods such as gas chromatography and high pressure liquid chromatography, which require sample extraction procedures and lengthy assay times. This is true of the fluorescence polarization immunoassay of the present invention, which combines the specificity of an immunoassay with the speed and convenience of a homogeneous method to offer a precise and reliable procedure for monitoring MHPG levels in urine or blood.

In a competitive binding immunoassay, the biological substance being measured (usually referred to as the "ligand") competes with a labeled reagent (the "ligand analog" or "tracer") for a limited number of receptor binding sites on antibodies specific to the ligand and ligand analog. The concentration of ligand in the sample determines the amount of ligand analog which binds to the antibody. The amount of ligand analog that will bind is inversely proportional to the concentration of ligand in the sample, because the ligand and the ligand analog each bind to the antibody in proportion to their respective concentrations.

MHPG is found both free and as sulfated and glucuronidated conjugates in urine. Only free MHPG will bind to antibody specific for MHPG. When MHPG from a urine sample or from a standard solution is equilibrated with MHPG tracer, the amount of MHPG tracer bound to the antiserum will be inversely proportional to the amount of free MHPG in the sample or standard. Thus, sulfated or glucuronidated conjugates must first be deconjugated to free MHPG if the competitive binding immunoassay is to provide an accurate quantitation of total MHPG present.

Fluorescence polarization is one method that may be utilized to measure the amount of tracer-antibody conjugate produced in a competitive binding immunoassay. Fluorescence polarization techniques are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the light remains highly polarized because the fluorophore is constrained from rotating between the time that light is absorbed and the time that it is emitted. In contrast, when an unbound tracer is excited by plane polarized light, its rotation is much faster than that of the corresponding tracer-antibody conjugate; as a result, the light emitted from the unbound tracer molecules is depolarized.

Fluorescence polarization immunoassay techniques are well known in the art; to date, however, the use of such techniques for the determination of urinary MHPG levels has not been successfully attempted. The present invention offers an advance in the art in that highly accurate determinations of the amount of MHPG in urine are obtainable with increased convenience, at decreased expense, without the disadvantages heretofore imposed by the various available assay systems.

SUMMARY OF THE INVENTION

The present invention is directed to a fluorescence polarization immunoassay for MHPG; to tracers, immunogens and antibodies for use in the assay; and to analytical methods for conducting the assay.

A first aspect of the invention relates to the discovery of certain tracers and immunogens having novel structures. Both the tracers and the immunogens can be represented by the structural formula shown in FIG. 2 of the drawings, wherein $R_1$ is OR', F, Br, Cl, I, $OPO_3H$, $OPO_3R'$, $OSO_2R'$,

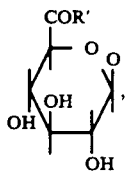

R—Z—Q;

$R_2$ is H when $R_1$ is R—Z—Q and is R—Z—Q when $R_1$ is not R—Z—Q;

$R_3$ is H, OH, $CH_3$ or $C_2H_5$;

R' is r-q, where r is a linking group including up to 7 heteroatoms and having a total of from 0 to 20 carbon atoms and heteroatoms arranged in a straight or branched chain and containing up to two ring structures, and q is H, CO or NH;

Q is a poly (amino acid), a poly (amino acid) derivative or another immunologically active carrier, or fluorescein or a fluorescein derivative;

Z is CO, NH, $CH_2NH$ or CS when Q is fluorescein or a fluorescein derivative and is N, NH, $SO_2$, $PO_2$, PSO or a glucuronide moiety when Q is a poly (amino acid), a poly (amino acid) derivative or another immunologically active carrier; and R is a linking group including up to 7 heteroatoms when Q is a poly (amino acid), a poly (amino acid) derivative or other immunologically active carrier and including up to 10 heteroatoms when Q is fluorescein or a fluorescein derivative, and having a total of from 0 to 20 carbon atoms and heteroatoms arranged in a straight or branched chain and containing up to two ring structures.

A second aspect of the invention relates to a method for preparing a tracer by coupling a compound of the structural formula shown above, where-in $R_1$ is OR', F, Br, Cl, I, $OPO_3H$, $OPO_3R'$, $OSO_2R'$,

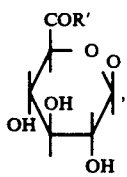

or R—Y;

$R_2$ is H when $R_1$ is R—Y and is R—Y when $R_1$ is not R—Y;

$R_3$ is H, OH, $CH_3$ or $C_2H_5$;

R' is r-q, where r is a linking group including up to 7 heteroatoms and having a total of from 0 to 20 carbon atoms and heteroatoms arranged in a straight or branched chain and containing up to two ring structures, and q is H, CO or NH;

Y is $NH_2$, COOH, $PO_3H$, $PSO_2H$, or

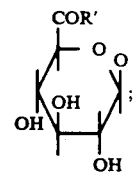

and

R is a linking group including up to 10 heteroatoms and having a total of from 0 to 20 carbon atoms and heteroatoms arranged in a straight or branched chain and containing up to two ring structures with fluorescein or a derivative of fluorescein with fluorescein or a derivative of fluorescein.

A third aspect of the invention relates to a method for preparing an immunogen by coupling a compound of the structural formula shown above, wherein $R_1$ is OR', F, Br, Cl, I, $OPO_3R'$, $OSO_2R'$,

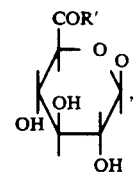

or R—X;

$R_2$ is H when $R_1$ is R—X and is R—X when $R_1$ is not R—X;

$R_3$ is H, OH, $CH_3$ or $C_2H_5$;

R' is r-q, where r is a linking group including up to 7 heteroatoms and having a total of from 0 to 20 carbon atoms and heteroatoms arranged in a straight or branched chain and containing up to two ring structures, X is $NH_2$, COOH, $PO_3H$, $PSO_2H$, or

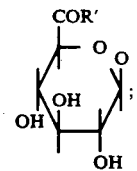

and

R is a linking group including up to 7 heteroatoms and having a total of from 0 to 20 carbon atoms and heteroatoms arranged in a straight or branched chain and containing up to two ring structures with a poly(amino acid), a derivative of a poly(amino acid) or other immunologically active carrier.

A fourth aspect of the invention relates to antibodies raised by the novel immunogens.

A fifth aspect of the invention relates to a novel stabilizing matrix for the tracers of the invention.

A sixth aspect of the invention relates to an improved specimen preparation method utilizing a metal silicate for reduction of specimen background and interfering metabolites.

A seventh aspect of the invention relates to an improved process for measuring MHPG. A sample is contacted with MHPG antiserum, the aforementioned metal silicate, and a fluorescein-containing MHPG derivative capable of producing a detectable fluorescence polarization response to the presence of the MHPG antiserum. Plane polarized light is then passed through the solution to obtain a fluorescence polarization response, and this response is detected as a measure of the total amount of MHPG in the sample. The improved process of this aspect of the invention allows for greatly increased specimen throughput as compared to such methods of the prior art as gas chromatography-electron capture and high performance liquid chromatography-electrochemical detection.

Further objects and attendant advantages of the invention will be best understood from a reading of the following detailed description taken together with the figures and the examples.

BRIEF DESCRIPTION OF THE DRAWINGS

In the following figures the symbol "Fl" represents a fluorescein moiety, "BSA" represents bovine serum albumin, and "KLH" represents keyhole limpet hemocyanin. The particular orientation of the benzylic hydroxyl group of the MHPG moiety in the figures is not meant to imply nor to exclude either possible enantiomer.

FIG. 1 shows the general structure of the metabolite MHPG to be quantitatively determined in accordance with the present invention.

FIG. 2 shows a general structural formula for the tracers and the immunogens of the present invention as well as the classes of reactants used in preparing them.

FIG. 3 shows the alternate structural formulae and names of the fluorescein moiety included in the tracers of the present invention.

FIGS. 4-1 to 4-12 show various linkages that couple the fluorescein moiety to the precursor in FIG. 2 when FIG. 2 represents a precursor for the tracer.

FIG. 5 shows the general structure for acetovanillone, the starting material for the synthesis of both the tracers and the immunogens of the present invention.

FIGS. 6 through 13 show precursors formed in the synthesis of both the tracers and the immunogens of the present invention.

DETAILED DESCRIPTION OF THE INVENTION

Figure 5:
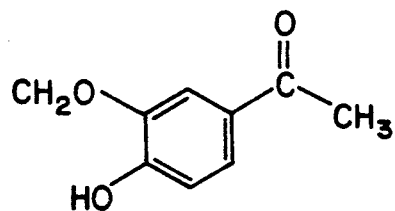

The present invention involves the use of fluorescein and derivatives of fluorescein. A necessary property of fluorescein and its derivatives for the usefulness of the tracer compounds herein is the fluorescence of fluorescein.

Fluorescein exists in either of two tautomeric forms, illustrated in FIG. 3, depending upon the acid concentration (pH) of the environment. In the open (acid) form, there are a number of conjugated double bonds which make that form of fluorescein (and compounds containing a fluorescein moiety) capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, allowing the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

The numbering of carbon atoms of the fluorescein molecule varies, depending upon whether the open or closed form of the molecule is considered. Accordingly, the literature concerning fluorescein and its compounds is not uniform as to carbon atom numbering. The numbering system used herein is illustrated in FIG. 3 as the lactone form of fluorescein.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer antibody complex assumes a value intermediate between that of the tracer and that of the tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture may be accurately determined.

The Reagents

Both the immunogens and the tracers of the present invention can be represented by the general structural formula shown in FIG. 2 of the drawings, wherein $R_1$ is OR', F, Br, Cl, I, $OPO_3H$, $OPO_3R'$, $OSO_2R'$,

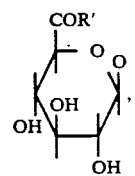

or R—Z—Q;

$R_2$ is H when $R_1$ is R—Z—Q and is R—Z—Q when $R_1$ is not R—Z—Q;

$R_3$ is H, OH, $CH_3$ or $C_2H_5$;

R' is r-q, where r is a linking group including up to 7 heteroatoms and having a total of from 0 to 20 carbon atoms and heteroatoms arranged in a straight or branched chain and containing up to two ring structures, and q is H, CO or NH;

Q is a poly (amino acid), a poly (amino acid) derivative or another immunologically active carrier, or fluorescein or a fluorescein derivative;

Z is CO, NH, $CH_2NH$ or CS when Q is fluorescein or a fluorescein derivative and is N, NH, $SO_2$, $PO_2$, PSO or a qlucuronide moiety when Q is a poly (amino acid), a poly (amino acid) derivative or another immunoloqically active carrier; and R is a linking group including up to 7 heteroatoms when Q is a poly (amino acid), a poly (amino acid) derivative or other immunoloqically active carrier and including up to 10 heteroatoms when Q is fluorescein or a fluorescein derivative, and having a total of from 0 to 20 carbon atoms and heteroatoms arranged in a straight or branched chain and containing up to two ring structures.

The objective is to have competition between MHPG and the tracer for the recognition sites of the antibody. Great variations in the structure of the tracers and haptens are allowed in achieving this goal. (For purposes of this disclosure, "haptens" are precursors of the immunogens comprising generally a substituted MHPG derivative bearing a group suitable for linking to an immunologically active carrier.)

The Structure of the Immunogens

Usable antibodies can be produced from a variety of MHPG derivatives. The present invention utilizes immunogens prepared from MHPG compounds functionalized at the 5-position, the site most distant from all metabolically active sites on the molecule.

The immunogens, then, are derived from the general structure shown in FIG. 2 and are prepared by coupling a compound of the class shown with a poly (amino acid), a poly (amino acid) derivative, or another immunologically active carrier as will be discussed in the context of the synthetic method.

In a preferred form of the invention, the immunogen is prepared by coupling the aforedescribed substituted MHPG compound with bovine serum albumin. Various other protein carriers may also be used to good advantage, e.g., keyhole limpet hemocyanin, egg ovalbumin, bovine gamma-globulin, thyroxine-binding globulin, and so forth. Alternatively, synthetic poly (amino acids) having a sufficient number of available amino groups can be employed, as can other synthetic or natural polymeric materials bearing functional groups reactive with MHPG.

The Structure of the Tracers

The tracers of the present invention are also derived from the general structure shown in FIG. 2. The tracer is an MHPG derivative that is linked to a fluorescein derivative by, for example, an amido aminoalkyl, thiourea, ether, thioether or oximo group, as shown in FIG. 4. The tracers are prepared by the appropriate fluorescein derivative to an MHPG derivative containing an amino, carboxylic acid or other appropriate group, as will be discussed in the context of the synthetic method and the examples. By way of example, any of the following fluorescein derivatives can be used:

| | |
|---|---|
| Fl—$CH_2$—$NH_2$ | aminomethyl fluorescein |
| Fl—$CO_2H$ | fluorescein amine |
| Fl—$CO_2H$ | carboxyfluorescein |
| Fl—$NHCOCH_2I$ | α-iodacetamidofluorescein |
| Fl—$NHCOCH_2Br$ | α-bromoacetamidofluorescein |

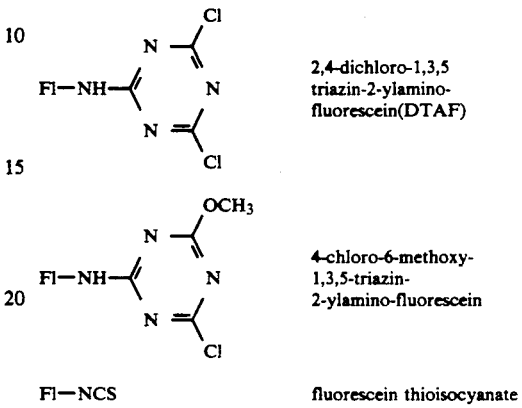

| | |
|---|---|
| Fl—NCS | fluorescein thioisocyanate |

The Antibodies

The antibodies of the present invention are prepared by eliciting a response in rabbits to the immunogens described supra. The immunogen is administered to animals or to in vivo cultures of immunocompetent cells by a series of inoculations, in a manner well known to those skilled in the art. It should be understood that although rabbits were the preferred immune host to MHPG immunogens in the experiments detailed herein, an in vivo or in vitro host capable of producing antibodies to the structures herein outlined may be employed.

Synthesis of the Immunogens

A ten-step synthetic route was developed for aspect, the route comprises preparation of the intermediate 4-(5-(1,2-dihydroxyethane)-2-hydroxy-3-methoxyphenyl)-2-butenoic acid by O-alkylation of acetovanillone at the 4-position by allyl bromide, a Claisen rearrangement in refluxinq N,N-dimethylaniline to 4-hydroxy-3-methoxy-5-(2-propenyl)-acetophenone oxidation by sodium periodate/osmium tetraoxide to 5-formylmethyl-4 hydroxy-3-methoxyacetophenone, Wittig reaction of the aldehyde with triethylphosphonoacetate, selective monobromination by cupric bromide in refluxing ethyl acetate/chloroform, formation of the diacetoxy compound with potassium acetate/acetic anhydride, reduction of the ketone with sodium borohydride, and hydrolysis of the ethyl ester with 1N sodium hydroxide. The N-hydroxysuccinimide ester of the resulting acid is then coupled with bovine serum albumin or keyhole limpet hemocyanin to form the immunogen.

Synthesis of the Tracers

The tracers may be prepared using the first six steps of the synthetic route outlined supra for synthesis of the immunogens, followed by acid hydrolysis of the ester and reduction of the ketone by sodium borohydride. The N-hydroxysuccinimide ester of the resulting acid thus prepared is then coupled with a fluorescein derivative, preferably aminomethylfluorescein, to form a tracer.

It should be noted that this synthetic route results in a mixture of two double-bond positional isomers of the hapten-to-fluorescein connecting arm. (Two double-bond positional isomers of the hapten-to-protein connecting arm also result from the immunogen synthesis, supra.) In isomer "A" the double bond was found to be conjugated to the carbonyl group of the arm, while in isomer "B" it was conjugated to the aromatic ring of MHPG. Testing of the two isomers with antibody resulting from mixed-isomer immunogen revealed the performance of isomer "A" to be significantly better than that of isomer "B" in terms of span. In view of this, two steps of the original synthetic route, supra, were modified in order to maximize the amount of isomer "A" produced in the preparation of the tracer. In this modified synthetic route, the diacetoxy compound is hydrolyzed with 6N hydrochloric acid and the resulting keto acid reduced with sodium borohydride to 5-(carboxyallyl)-MHPG. Coupling of the active ester to aminomethylfluorescein resulted in a 3:2 ratio of isomer "A" to isomer "B".

The Assay

The particular tracers, antibodies and additional reagents of the present invention have been found to accurately and specifically measure total MHPG levels in urine. In accordance with the analytical methods of the invention, i.e., the methods of determining MHPG by a fluorescence immunoassay procedure using the tracer compounds and immunogens of the invention, a sample containing or suspected of containing MHPG is intermixed with a biologically acceptable salt of the tracer and an antibody specific to both MHPG and the tracer.

In a preferred embodiment of the invention, the reagents include a pretreatment reagent package consisting of glusulase, hydrolysis buffer, a resin mix, and extraction reagent and a reagent test pack consisting of a fluorescent-labeled MHPG (tracer), antibody specific for MHPG and the pretreatment reagent. Urinary MHPG is first deconjugated enzymatically, so that all MHPG present is in the form of free MHPG rather than sulfated or glucuronidated conjugates, and is subsequently extracted with magnesium silicate resin before the fluorescent-labeled MHPG tracer is added.

Antibody produced using the immunogen described above is added, and free MHPG competes with the fluorescent tracer for limited antibody sites, resulting in the formation of complexes. By maintaining constant the concentration of tracer and antibody, one can assure that the ratio of MHPG-antibody complex to tracer-antibody complex that is formed will be directly proportional to the total amount of MHPG in the sample. Therefore, upon exciting the mixture with linearly polarized light and measuring the polarization of the fluorescence emitted by a tracer and a tracer-antibody complex, one is able to determine quantitatively the total amount of MHPG in the sample.

The results can be quantified in terms of net millipolarization units, span (in millipolarization units) and relative intensity. The measurement of millipolarization units indicates the maximum polarization when a maximum amount of the tracer is bound to the antibody in the absence of any free MHPG. The higher the net millipolarization units, the better the binding of the tracer to the antibody. The span is an indication of the difference between the net millipolarizations at the points of maximum and minimum amount of tracer bound to the antibody. A larger span provides for a better numerical analysis of data. The intensity is a measure of the strength of the signal above background. Thus, a higher intensity will give a more accurate measurement. The intensity is determined at about 300 to 500 nanomolar for the preferred tracers of the invention, as the sum of the vertically polarized intensity plus twice the horizontally polarized intensity. The intensity of the tracer signal can range from about three times to about thirty times the background noise, depending upon the concentration of the tracer and other assay variables.

The preferred method of the improved assay of the present invention will now be discussed in detail. The assay is a "homogeneous assay", which means that the end polarization readings are taken from a solution in which bound tracer is not separated from unbound tracer. This is a distinct advantage over heterogeneous immunoassay procedures wherein the bound tracer must be separated from the unbound tracer before a reading can be taken.

The pH at which the method of the present invention is practiced must be sufficient to allow the fluorescein moiety of the tracers to exist in their open form. The pH may range from about 5 to 10, more preferably in the range of from about 6 to 9, and most desirably from about 7.0 to 7.5. Relatively small changes in pH radically affect the intensity and special characteristics of fluorescence.

Various buffers may be used to achieve and maintain the pH of the homogeneous immunoassay of the present invention during the assay procedure. Representative buffers include borate, citrate, acetate phosphate, carbonate, tris, barbital and the like. The particular buffer employed is not critical to the present invention, but the tris and phosphate buffers are preferred. The cation portion of the buffer will generally determine the cation portion of the tracer salt in solution.

The reagents for the fluorescence polarization assay of the present invention comprise antibody specific for MHPG and tracer. Additionally, largely conventional solutions including an MHPG pretreatment solution, a dilution buffer, MHPG calibrators and MHPG controls are desirably prepared. Typical solutions of these reagents, some of which are described herein, are commercially available in assay "kits" from Abbott Laboratories, Abbott Park, Ill.

All percentages expressed herein are weight/volume unless otherwise indicated. The tracer formulation presently preferred is 430 nanomolar tracer in 25% dimethylsulfoxide (volume/volume), 75% ethylene glycol (volume/volume), 1% sodium chloride, 0.1% sodium metabisulfite, and 0.1% sodium azide. The antiserum formulation is comprised of rabbit serum diluted with 1% hydrolyzed ovalbumin in phosphate-buffered saline and 0.1% sodium azide. The pretreatment formulation is comprised of sodium dodecyl sulfate in 0.05M tris at pH 7.5 and 0.1% sodium azide. Calibrators are comprised of MHPG in an artificial urine matrix at concentrations of 0.0, 0.38, 0.75, 1.5, 3.0 and 6.0 with 0.1% sodium azide as preservative. Controls are comprised of MHPG in an artificial urine matrix at the concentrations of 0.5, 1.0, and 2.0 with 0.1% sodium azide as a preservative.

The pretreatment reagents preferred to hydrolyze MHPG conjugates and decrease background intensity and interference are acetate buffer, glusulase, hydrochloric acid/sodium chloride solution, and magnesium silicate. The acetate buffer is comprised of disodium EDTA, bovine gamma globulin and sodium azide in ammonium acetate at pH 6.0. Glusulase, a crude enzyme preparation which can be obtained from *Helix pomatia* and contains both sulfatase and glucuronidase activities, was obtained from Sigma Chemicals, St. Louis, Miss. The enzyme contains sodium azide as a preservative. Sample background is decreased using 3M hydrochloric acid which has been 80% saturated with sodium chloride. The resin is magnesium silicate, 100-200 mesh, obtained from Floridin, Pittsburgh, Pa.

The preferred procedure is especially designed to be used in conjunction with the Abbott TDx ® polarization analyzer available from Abbott Laboratories, Irving, Tex. Four hundred microliters of urine are required. The calibrators, controls, or unknown samples are pipetted into a microcentrifuge tube, followed by acetate buffer and glusulase. After incubation, resin and acid solution are added to the microcentrifuge tube, which is then vortexed and centrifuged. At least 340 ul of the supernatant is transferred to the sample well of the TDx ® sample cartridge. If a TDx ® MHPG assay kit is being used with the TDx ® analyzer, the sample cartridges are placed directly into a sample carousel, the caps from each of the three reagent containers in the kit are removed and the reagent pack is placed into its designated well inside the TDx ® analyzer. From this point, the procedure is fully automated.

The fluorescence polarization value of each calibrator, control or sample is determined and is printed on the output tape of an instrument such as the Abbott TDx ® polarization analyzer. A standard curve is generated in the instrument by plotting the polarization of each calibrator versus its concentration using nonlinear regression analysis. The concentration of each control or sample is read off the stored calibration curve and printed on the output tape.

If a manual assay is being performed, then the sample is mixed with the pretreatment solution, a portion of the antiserum, and dilution buffer, and a background reading is taken. The remaining antiserum is then mixed with the sample. The tracer is then finally added to the test solution. After incubation, a fluorescence polarization reading is taken.

With respect to the foregoing preferred procedure, it should be noted that the tracer, antibody, pretreatment solution, calibrators and controls should be stored between about 2 and about 8 degrees C, while the dilution buffer should be stored at ambient temperature. A standard curve and controls should be run every two weeks, with each calibrator and control run in duplicate. Controls should be run daily and all samples can be run in replicates if so desired.

It should be understood that the foregoing detailed description and the following examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples I through XXIII describe experiments that were performed in accordance with the concepts of the present invention. Examples I through XII are directed to the synthesis of precursors for immunogens; Examples IX and X are directed to the preparation of immunogens useful for producing antibody; Examples I through VI and XI through XIII are directed to the synthesis of precursors for tracers; and Examples XIV and XV are directed to the preparation of tracers. Example XVI illustrates one preferred immunoassay embodiment. Examples XVII and XVIII compare the accuracy of the method of the invention vis-a-vis other methods. Example XV illustrates the improved specimen preparation step.

EXAMPLE I

Figure 6:
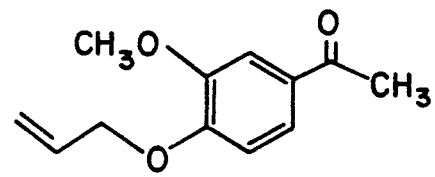

This example illustrates the synthesis of 3-methoxy-4-(1 propenyloxy)-acetophenone, shown in FIG. 6.

A 500 ml three-necked round bottom flask was equipped with a stopper, a 125 mL addition funnel containing 20.0 g (118 mmol) of acetovanillone dissolved in 80 mL of dimethylformamide, a rubber septum, and a magnetic stir bar. After the system was purged with 10 nitrogen, 4.72 g (1.equiv.) of sodium hydride was added to the pot and washed with hexanes (3×50 mL; dried over 3 angstrom sieves). After removal of the hexanes by syringe, 120 mL of dimethylformamide was injected and the resulting sodium hydride suspension was stirred. The acetovanillone solution was added dropwise over 15 minutes and the resulting solution stirred an additional 10 minutes. Neat allyl bromide (21.40 g, 1.5 equiv) was then injected and the reaction allowed to stir for 24 hours at room temperature under nitrogen. The reaction was monitored by thin-layer chromatography.

The reaction was then diluted with hexanes (1 L), washed with water (3×200 mL), 1N sodium hydroxide (2×200 mL) and saturated sodium chloride (2×100 mL), dried over anhydrous magnesium sulfate, vacuum filtered and rotary evaporated in vacuo to a yellow oil. Further removal of solvent on high vacuum afforded 12.24 g (59.3 mmol) of the desired material (50% yield).

EXAMPLE II

Figure 7:
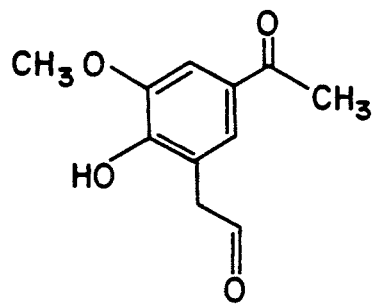

This example illustrates the synthesis of 4 hydroxy-3-methoxy-5-(1-propenyl)-acetophenone, shown in FIG. 7.

6.02 g (29.2 mmol) of 4-O-allylacetovanillone (prepared in Example I) and 250 mL of N,N dimethylaniline were combined in a 500 mL round bottom flask equipped with a condenser and refluxed under nitrogen for 6 hours. The reaction was cooled to room temperature and then worked up as follows: dilution with hexanes (500 mL), extraction with 1N sodium hydroxide (4×100 mL), acidification of the aqueous with concentrated hydrochloric acid to a pH between 0 and 1, and extraction with hexanes/diethyl ether (3:1 volume/volume; 3×200 mL). The organic was washed with 3N hydrochloric acid (3×100 mL) and saturated sodium chloride (2×100 mL), then dried over anhydrous magnesium sulfate, vacuum filtered and rotary high-vacuum afforded 5.23 g (25.3 mmol) of the desired beige powder (87% yield).

EXAMPLE III

Figure 8:
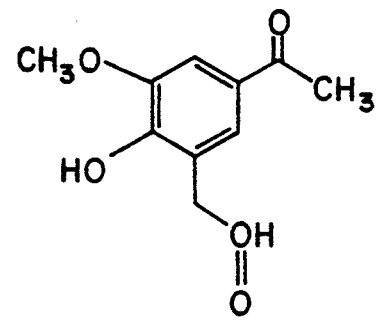

This example illustrates the synthesis of 5-formylmethyl 4-hydroxy-3-methoxyacetophenone, shown in FIG. 8.

1.0 g (4.85 mmol) of 4-hydroxy-3-methoxy-5-(1 propenyl)-acetophenone (prepared in Example II) was dissolved in 25 mL of tetrahydrofuran and 20 mL of distilled water. 1.17 g of solid sodium periodate and 2.5 mL of osmium tetroxide/tetrahydrofuran solution (1 g osmium tetroxide/50 mL tetrahydrofuran) were added, and the resultant mixture was allowed to stir at room temperature under nitrogen in a 100 mL round bottom flask for 30 minutes. Another equivalent of sodium periodate was then added, and the mixture was allowed to stir for 1 hour.

The resultant goldenrod-colored mixture was diluted with 300 mL of diethyl ether and 150 mL of distilled water, whereupon the layers were separated and the aqueous extracted with diethyl ether (150 mL) and ethyl acetate (2×200 mL) The combined organics were washed with saturated sodium chloride (2×100 mL) and dried over anhydrous magnesium sulfate. The mixture was vacuum filtered and rotary evaporated in vacuo (ambient bath).

The resultant dark orange oil was dissolved in ethyl acetate, applied to a silica gel chromatography column, covered with sand, and eluted with 50:50 ethyl acetate/hexanes at a rate of 1 mL/minute. Product-containing fractions were identified by thin-layer chromatography, combined and rotary evaporated in vacuo to total 666 mg of a light greenish-yellow oil (3.2 mmol, 66% yield). It should be noted that the foregoing reaction is preferably run on no larger than a 1.0 g scale. Also, this aldehyde is particularly unstable and should be used in the Wittig reaction the same day it is made, or kept on high vacuum to prevent oxidation.

EXAMPLE IV

Figure 9:
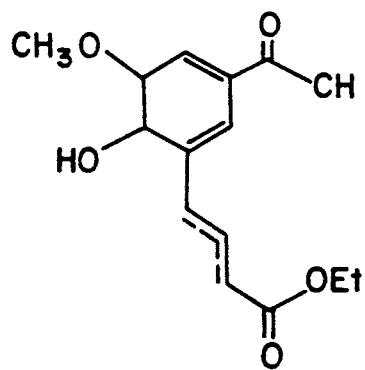

This example illustrates the synthesis of ethyl-4-(5-acetyl-2-hydroxy-3-methoxyphenyl)-2-butenoate, shown in FIG. 9.

114 mg (1 equiv) of sodium hydride (60% oil dispersion) was suspended in tetrahydrofuran (10 mL) in a 50 mL round bottom flask equipped with a 25 mL addition funnel and an inlet valve for a nitrogen purge. The addition funnel contained 593.6 mg (2.85 mmol) of the 5-formylmethyl-4-hydroxy-3methoxyacetophenone (prepared in Example III, supra) dissolved in 15 mL tetrahydrofuran. This solution was dripped into the stirred sodium hydride suspension over a 10-minute period, then allowed to stir for 10 minutes under nitrogen. An additional equivalent of sodium hydride and 671 mg (1.05 equiv) of neat triethyl phosphonoacetate were added, and allowed to stir for 15 minutes. The brick-red mixture was then quenched with acetic acid (300 l).

The reaction was next diluted with 100 mL of diethyl ether and 200 mL of distilled water, the layers were separated, and the aqueous layer was extracted with methylene chloride (2×100 mL). The combined organics were washed with saturated sodium hydrogen carbonate (2 ×100 mL) and saturated sodium chloride (200 mL), dried over anhydrous magnesium sulfate, vacuum filtered, and rotary evaporated in vacuo to a yellow oil.

The oil was dissolved in methylene chloride, applied to a silica gel chromatography column, covered with sand, and eluted with 40:60 ethyl acetate/hexanes. The product-containing fractions were identified by thin-layer chromatography, combined and rotary evaporated in vacuo to a colorless oil. Further removal of solvent on high-vacuum gave the desired material. It should be noted that this reaction resulted in a mixture of the double bond positional isomers, designated "A" and "B".

EXAMPLE V

Figure 10:
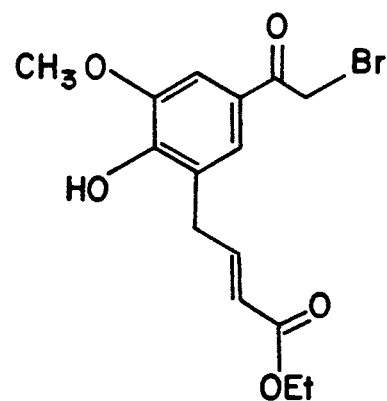

This example illustrates the synthesis of ethyl4-(5-bromoacetyl-2-hydroxy-3-methoxyphenyl)-2-butenoate, shown in FIG. 10.

7.43 mmol of the ethyl-4-(5-acetyl-2-hydroxy-3-methoxyphenyl)-2-butenoate (prepared in Example IV, supra), 3.35 g (2 equiv) of cupric bromide, 40 mL of chloroform, and 40 mL of ethyl acetate were combined in a 250 mL round bottom flask equipped with a condenser and refluxed for 1.5 hours. The reaction was monitored by thin-layer chromatography. The reaction was then cooled to room temperature, whereupon the mixture was distributed to centrifuge tubes and centrifuged, and the supernatant decanted. The precipitate was washed with methylene chloride. The combined wash solution was rotary evaporated in vacuo to a yellow oil.

The oil was dissolved in methylene chloride, applied to a silica gel chromatography column, covered with sand, and eluted with 40:60 ethyl acetate/hexanes. The product-containing fractions were combined and rotary evaporated in vacuo to afford 2.103 g (5.9 mmol) of the desired product (79% yield).

EXAMPLE VI

Figure 11:
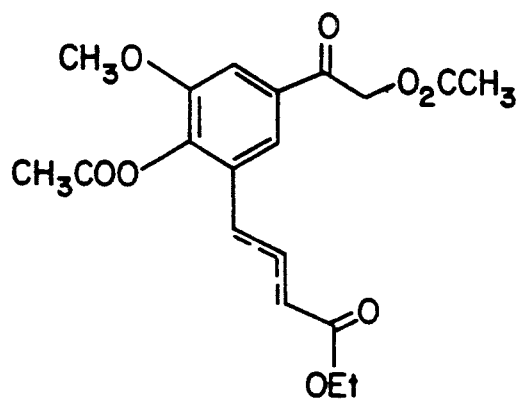

This example illustrates the synthesis of ethyl4-(5-acetoxyacetyl-2-acetoxy-3-methoxyphenyl)-2-butenoate, shown in FIG. 11.

2.1065 g (5.9 mmol) of the ethyl-4-(5-bromoacetyl-2-hydroxy-3-methoxyphenyl)-2-butenoate (prepared in Example V, supra), 607.8 mg (1.05 equiv) of potassium acetate, and 30 mL of acetic anhydride were combined in a 100 mL flask equipped with a stopper and were stirred in an oil bath (90° C.). The reaction was monitored by silica gel thin-layer chromatography; typically, it will be complete after 60 minutes.

The mixture was rotary evaporated in vacuo, redissolved in methylene chloride (300 mL) and washed with saturated sodium chloride (2×200 mL). The organic was dried over anhydrous magnesium sulfate, vacuum filtered, and rotary evaporated in vacuo to a small volume. The acetic anhydride was removed by azeotroping with toluene in vacuo. Further solvent removal on high vacuum afforded the desired solid (quantitative).

EXAMPLE VII

Figure 12:
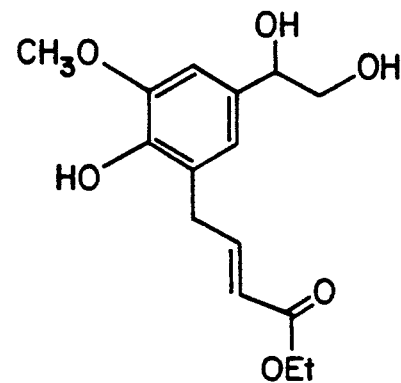

This example illustrates the synthesis of ethyl4-(5-(1,2-dihydroxyethane)-2-hydroxy-3-methoxyphenyl)-2-butenoate, shown in FIG. 12.

828.8 mg (2.19 mmol) of the ethyl-4-(5-acetoxyacetyl-2-acetoxy 3-methoxyphenyl)-2-butenoate (prepared in Example VI, supra), was dissolved in 4 mL of tetrahydrofuran. To this was added 7.7 mL (0.35 equiv.) of sodium borohydride solution (0.1M in isopropyl alcohol) and isopropyl alcohol (6.4 mL). The resultant mixture was allowed to stir at room temperature for 20–30 minutes. The progress of the reaction was followed by thin-layer chromatography (silica gel; 50:50 ethyl acetate/hexanes; reaction spot quenched with acetone). Upon completion of the reaction, 30 mL of acetone was added to quench the reaction. After 15 minutes of stirring; the mixture was rotary evaporated in vacuo to a dark orange oil. No workup or purification was necessary. The material was kept on high vacuum until needed.

EXAMPLE VIII

Figure 13:
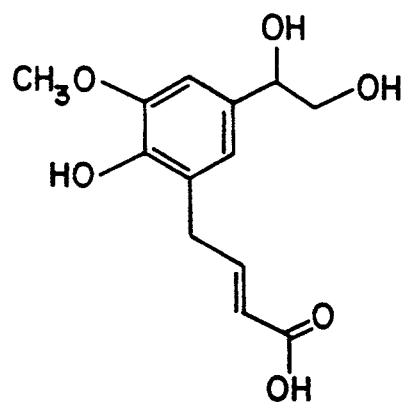

This example illustrates the synthesis of 4 (5 (1,2-dihydroxyethane)-2-hydroxy-3-methoxyphenyl)-2-butenoic acid, shown in FIG. 13.

2.19 mmol of the ethyl-4-(5-(1,2 dihydroxyethane)-2-hydroxy-3-methoxyphenyl (prepared in Example VII, supra) was dissolved in 30 mL of p-dioxane. 12 mL (5.5 equiv) of 1M sodium hydroxide was added and allowed to stir at room temperature for 1.5 hours. The progress of the reaction was followed by thin-layer chromatography (silica gel; 15:85 methanol/methylene chloride+0.5% acetic acid).

Upon completion, the reaction was acidified with 3N hydrochloric acid to a pH of 2-3. Following dilution with saturated sodium chloride (200 mL) and extraction with ethyl acetate (3×200 mL), the reaction was dried over anhydrous magnesium sulfate, vacuum filtered, and rotary evaporated in vacuo. The crude was placed on high vacuum.

654.4 mg of the crude foam was dissolved in methylene chloride (with a small percentage of methanol), applied to a silica qel chromatography column (230-400 mesh; 15:85 methanol/methylene chloride), covered with sand, and eluted with 15:85 methanol/methylene chloride+0.5% acetic acid. Following collection of 3 mL fractions, the product-containing fractions were identified by thin-layer chromatography, combined and rotary evaporated in vacuo, stripping with 100 mL toluene to azeotrope acetic acid. The resultant yellowish-white solid was placed on high vacuum to afford 389.5 mg (11.45 mmol) of the desired product (66% yield).

EXAMPLE IX

Figure 14:
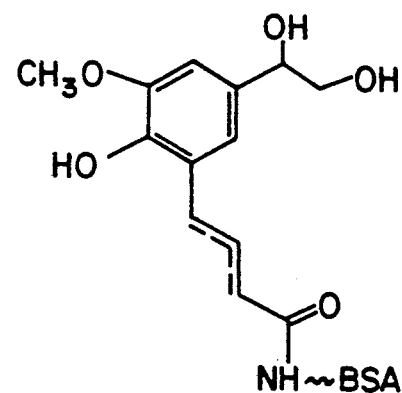
FIGS. 14 and 15 show immunogens in accordance with the present invention.

This example illustrates the coupling of 4-(5-(1,2-dihydroxyethane)-2-hydroxy-3-methoxyphenyl)-2-butenoic acid to bovine serum albumin and corresponds to FIG. 14.

127.8 mg (0.48 mmol) of the 4-(5-(1,2-dihydroxyethane)-2-hydroxy-3-methoxyphenyl)-2-butenoic acid (prepared in Example VIII, supra) was dissolved in 3.8 mL of dimethylformamide. 109.2 mg (1.1 equiv) of 1,3-dicyclohexylcarbodiimide and 64.2 mg (1.2 equiv) of N-hydroxysuccinimide were added and allowed to stir at room temperature under nitrogen overnight to form an active ester.

182.8 mg of bovine serum albumin (BSA) was dissolved in 4 mL of distilled water and 1.8 mL of p-dioxane. The pH was adjusted to 8-9 with 2:1 saturated sodium bicarbonate: 5% sodium carbonate (2:1 by volume). The active ester solution was filtered through a cotton-plugged pipette into the BSA solution, washing with dioxane (900 1), dimethylformamide (600 1) and distilled water (2.7 mL). The pH was readjusted to approximately 8-9 and allowed to stir in a capped 20 mL scintillation vial overnight. After 12 hours, the reaction mixture was transferred to a dialysis bag (15.9 mm in diameter; 12-14,000 M.W. cutoff) and was dialyzed against 4 L of distilled water for 5 days (daily water changes). The contents of the bag were then transferred to a 300 mL lyophilization jar, frozen in an isopropanol/dry ice bath, and placed on a lyophilizer for 3 days. This afforded 148.2 mg of immunogen.

The conjugate was analyzed by trinitrobenzenesulfonic acid (TNBS) titration as follows: A blank solution was prepared by combining 1 mL of 4% sodium bicarbonate, 1 mL water, and 1 mL 0.1% TNBS. A standard solution was prepared by combining 0.5 mL of 4% sodium bicarbonate, 0.5 mL of a 1 mg/mL BSA solution in 4% sodium bicarbonate, and 0.5 mL of 0.1% TNBS. Immunogen solution was prepared by combining 0.5 mL of 4% sodium bicarbonate, 0.5 mL of a 1 mg/mL immunogen solution in 4% sodium bicarbonate, and 0.5 mL 0.1% TNBS. The three solutions were incubated in a water bath at 40° C. for 2 hours. The reaction was quenched with 10% sodium dodecyl sulfate (0.5 mL) and 1N hydrochloric acid (0.25 mL). (Note: 2x volume was used for the blank solution.) The UV absorbance at 335 nm was read as 1.60 for BSA (average of 3 solutions) and 0.264 for the immunogen, giving a value of 83.5% substitution by the hapten of amino groups on BSA of the immunogen.

EXAMPLE X

Figure 15:
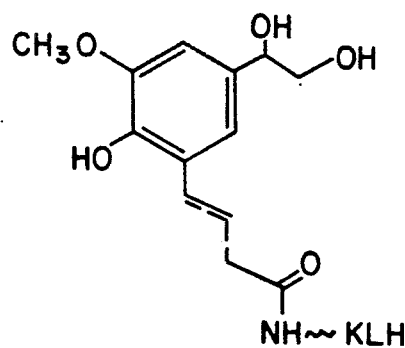

This example illustrates the coupling of 4-(5-(1,2-dihydroxyethane)-2-hydroxy-3-methoxyphenyl)-2-butenoic acid to keyhole limpet hemocyanin (KLH) and corresponds to FIG. 15.

88 mg (0.33 mol) of 4-(5-(1,2-dihydroxyethane)-2-hydroxy-3-methoxyphenyl)-2-butenoic acid (prepared in Example VII, supra) was dissolved in 2.8 ml N,N-dimethylformamide. 45.3 mg (1.2 equiv) N-hydroxysuccinimide and 75.2 mg (1.1 equiv) 1,3-dicyclohexylcarbodiimide were added and allowed to stir at room temperature under nitrogen overnight to form the N-hydroxysuccinimide active ester. 125 mg of keyhole limpet hemocyanin (KLH) was dissolved in 2.8 mL distilled water and 1.3 ml p-dioxane. The pH was adjusted to 8.5 with 2:1 (volume/volume) saturated sodium bicarbonate: 5% sodium carbonate. The active ester solution was filtered through a cotton-plugged pipette into the KLH solution, washing with distilled water (1.9 mL) and p-dioxane (0.6 mL). The pH was readjusted to 8.5 and allowed to stir under nitrogen overnight. The reaction mixture was transferred to a dialysis bag (14.6 mm in diameter; 12-14,000 m.w. cutoff) and was dialyzed against 4L of distilled water for 4 days (daily water changes). The contents of the bag were then transferred to a 300 mL lyophilization jar, frozen in an isopropanol/dry ice bath, and placed on a lyophilizer for 3 days. This afforded the immunogen as a light beige powder (114.6 mg). The immunogen was analyzed by ultraviolet spectroscopy.

EXAMPLE XI

Figure 16:
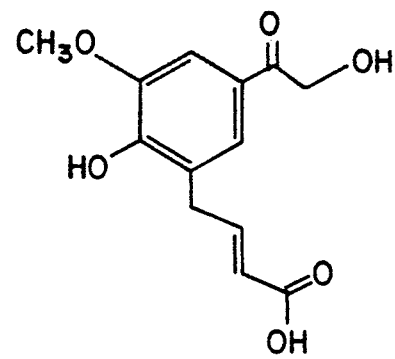
FIGS. 16 and 17 show additional precursors formed in the synthesis of the tracers.

This example illustrates the synthesis of 4-(5-hydroxyacetyl-2-hydroxy-3-methoxyphenyl)-2-butenoic acid, shown in FIG. 16.

1.1165 g (2.95 mmol) of the ethyl-4-(5-acetoxyacetyl 2-acetoxy-3-methoxyphenyl)-2-butenoate (prepared in Example VI, supra) was dissolved in 25 mL of p-dioxane. 12.5 mL of 6N hydrochloric acid was added, and the reaction was allowed to stir under a reflux condenser at 100° C. The reaction was monitored by thin layer chromatography (silica qel; 15:85 methanol/methylene chloride+0.5% acetic acid) and was essentially complete after 1.5 to 2 hours.

The reaction was then cooled to room temperature, diluted with saturated sodium chloride (300 mL) and extracted with ethyl acetate (3×150 mL). The organic was dried over anhydrous magnesium sulfate, vacuum filtered, and rotary evaporated in vacuo.

The oil was dissolved in methylene chloride, applied to a silica gel chromatography column (230-400 mesh; 150 g silica packed in 4 cm column with 7:93 methanol/methylene chloride, covered with sand, and eluted with 7:93 methanol/methylene chloride, +0.5% acetic acid. Product-containing fractions were combined, rotary evaporated in vacuo, and azeotroped with toluene. Drying on high vacuum afforded the desired yellow solid with the desired positional isomer in predominance (297.6 mg, 1.12 mmol, 38% yield).

EXAMPLE XII

This example illustrates the synthesis of 4-(5-(1,2-dihydroxyethane)-2-hydroxy-3-methoxyphenyl)-2-butenoic acid, shown in FIG. 13.

290.8 mg (1.09 mmol) of the 4-(5-hydroxyacetyl-2-hydroxy-3-methoxyphenyl)-2-butenoic acid (prepared in Example VI, supra) was dissolved in 6.3 mL of tetrahydrofuran. 10.9 mL (1 equiv) of a 0.1M isopropanol solution of sodium borohydride was added, and the resultant mixture was allowed to stir under a drying tube. The reaction was monitored by thin-layer chromatography (silica gel, 15:85 methanol/methylene chloride +0.5% acetic acid). After 1 hour, an additional equivalent of sodium borohydride was added. The reaction was quenched after 4 hours with 1N hydrochloric acid to a pH of approximately 1.

The reaction was then diluted with 250 mL of saturated sodium chloride and extracted with ethyl acetate (8×100 mL). The organic was dried over anhydrous magnesium sulfate, vacuum filtered, and rotary evaporated in vacuo to a yellow oil.

The oil was dissolved in 15:85 methanol/methylene chloride, applied to a silica gel chromatography column (80 g packed in 2 cm column with 15:85 methanol/methylene chloride), covered with sand, and eluted with 15:85 methanol/methylene chloride +0.5% acetic acid at 0.9 mL/minute (10 mL/fraction). Product-containing fractions were identified by thin-layer chromatography, combined and rotary evaporated in vacuo, azeotroping acetic acid with toluene. High vacuum afforded 198.7 mg (0.74 mmol) of the desired material (68% yield).

EXAMPLE XIII

Figure 17:
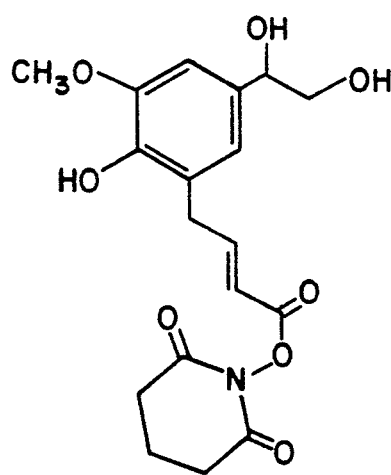

This example illustrates the synthesis of N-hydroxysuccinimide-active ester of 4-(5-(1,2-dihydroxyethane)-2-hydroxy-3-methoxyphenyl)-2-butenoic acid (prepared in Example XII, supra). The ester is shown in FIG. 17.

198.7 mg (0.74 mmol) of the compound prepared in Example XII was dissolved in 7.5 mL of dimethylformamide. 169.8 mg (1.1 equiv) of 1,3-dicyclohexylcarbodiimide and 102.3 mg (1.2 equiv) of N-hydroxysuccinimide were added, and the reaction was allowed to stir under nitrogen for 17 hours. This solution was used in the following example.

EXAMPLE XIV

Figure 18:
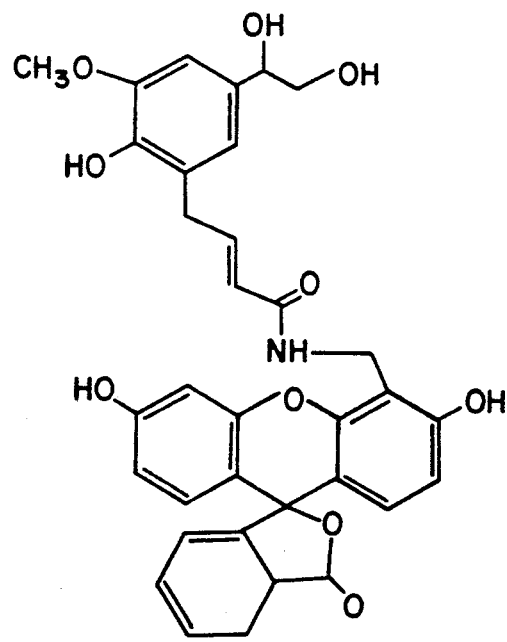
FIG. 18 shows a preferred tracer.

This example illustrates the synthesis of N-[4 (5-(1,2-dihydroxyethane)-2-hydroxy-3-methoxyphenyl)-2-butenoyl]-4'-aminomethylfluorescein tracer, shown in FIG. 18.

294 mg (1 equiv) of aminomethylfluorescein hydrochloride was dissolved in 2.2 mL of dimethyl formamide. To this was added the active ester solution prepared in Example XIII, which had been filtered while washing with 2×250 uL of dimethylformamide. The pH was adjusted to approximately 8–8.5 with triethylamine, resulting in a brick-red color. The reaction was stirred under nitrogen at room temperature, using thin-layer chromatography (silica gel, 10:90 methanol/methylene chloride +0.5% acetic acid) to monitor the reaction progress. Two elutions were performed to separate the "A" and "B" tracers resulting from the double bond positional isomers. Formation of the less desirable "B" tracer was initially observed, but the A:B ratio was approximately 50:50 after 1 hour. After 7 hours, when the A:B ratio was approx 60:40, the reaction was quenched with acetic acid, with the pH of the solution approximating 4.

The solution was then rotary evaporated under high vacuum to remove the dimethylformamide and placed in vacuo for 2 hours.

The resulting oil was dissolved in methanol (1.5 mL). 250 uL was applied to each of six 2-mm thickness silica qel preparative thin-layer chromatography plates. The plates were dried in a vacuum oven (no heat, high vacuum) for 1.5 hours, then developed in 10:90 methanol/methylene chloride +0.5% acetic acid. The tracer band (A+B) was scraped from each plate into a mortar, powderized, suspended in methylene chloride, and poured into a 4 cm i.d. chromatography column (plugged with cotton). After the methylene chloride was forced off with air pressure, the sorbent was washed with 10:90 methanol/methylene chloride +0.5% acetic acid (250 mL) into a 500 mL round bottom flask. The sorbent was then rotary evaporated in vacuo, the acetic acid was azeotroped with toluene, and the yellowish-orange powder was placed on high vacuum. Crude weight was 305 mg.

EXAMPLE XV

This example illustrates the high pressure liquid chromatography (HPLC) separation of tracer isomer "A", N-[4-(5-(1,2 dihydroxyethane)-2-hydroxy-3-methoxyphenyl)-2-butenoyl]-4'-aminomethylfluorescein, and tracer isomer "B", N [4-(5-(1,2-dihydroxyethane)-2-hydroxy-methoxyphenyl)-3-butenoyl]-4'-aminomethylfluorescein (prepared in Example XIV, supra). The HPLC system consisted of a 50-centimeter 10-micron particle size silica gel column, a guard column packed with pellicular silica gel, a pump, an ultraviolet detector set for a wavelength of 240 nonmeters, and an injector with a 200 uL injection loop. A 0.5–1.5/100 mL solution of the crude tracer in 10:90 methanol:methylene chloride containing one drop of acetic acid per 25 mL was injected into the column (injection size 200 uL) and was eluted with 4:96 methanol:methylene chloride +0.5% acetic acid at 4 mL/minute. This system gave the following values for the two isomers: retention time $t_o=43.5$ minutes ($K'a=7.4$), retention time $t_0=50.7$ minutes ($K'b=8.8$), resolution $R_s=1.6-1.7$. The eluent containing each isomer was rotary evaporated in vacuo to remove solvent and azeotroped with toluene to remove acetic acid. Each isomer was dried under high vacuum, then stored under nitrogen in a freezer.

EXAMPLE XVI

This example illustrates one preferred immunoassay embodiment.

MHPG-AMF was synthesized as described in Examples XIV and XV, supra. The tracer was dissolved in methanol, 200 uL of the stock solution was added to 10 mL of the DMSO/ethylene glycol matrix. 1.6 mL of the resulting stock solution was diluted in 100 mL of the DMSO/ethylene glycol matrix to give a tracer concentration of 430 nanomolar. One part of antiserum 1729 was diluted in 17 parts of phosphate-buffered saline solution containing 1% ovalbumin.

400 uL of each calibrator were incubated for 3 hours at 56° C. with 150 uL of acetate buffer and 30 uL lusulase. Approximately 0.1 g of magnesium silicate resin was added, followed by 100 uL of 80% sodium chloride-saturated 3M hydrochloric acid. The sample was vortexed for 1 minute and centrifuged.

Supernatant was mixed in the cuvette with antiserum and pretreatment reagent. After 4 minutes a fluorescent sample background reading was taken.

Remaining supernatant antiserum and tracer were transferred to the cuvette. After an incubation period, a final reading was taken and the MHPG concentration values were stored as a standard curve.

Figure 19:
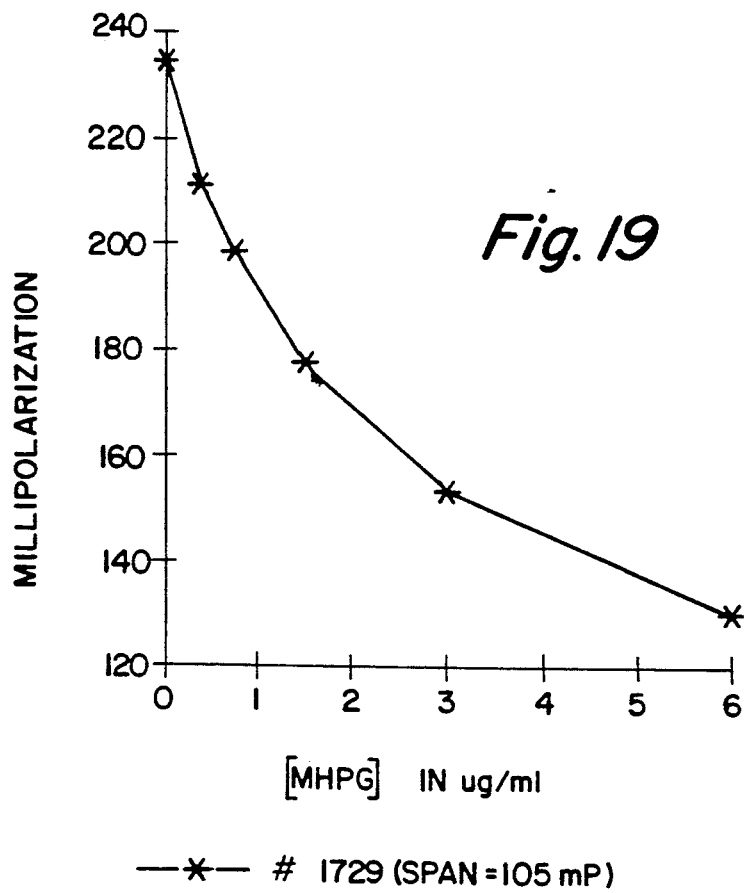
FIG. 19 shows the results of a preferred immunoassay embodiment.

The results are shown in FIG. 19.

EXAMPLE XVII

This example illustrates the accuracy of the method of the present invention vis-a-vis the primary method currently in use, gas chromatography with electron capture detection (GC-EC).

GC-EC vs. TDx (n=20)

Intercept=0.07
Slope=1.01
Coefficient of correlation=0.796

EXAMPLE XVIII

This example illustrates the accuracy of the method of the present invention vis a-vis high performance liquid chromatography with electron capture detection (HPLC-EC).

HPLC-EC vs. TDx (n=51)

Intercept=0.44
Slope=0.80
Coefficient of correlation=0.788

EXAMPLE XIX

This example, wherein 5 urine samples are spiked with MHPG and the percentage of the spike recovered in each instance is determined, further assesses the accuracy of the assay of the present invention.

An aliquot of each urine sample was spiked with 60 ug MHPG/mL using a concentrated stock of MHPG: 300 to 600 ug/mL. The sample was serially diluted with aliquots of the same sample until the following concentrations of added MHPG were obtained: 3.0, 1.5, 0.75, 0.38 ug/mL. Enzymatic hydrolysis and pretreatment were performed as described in Example XVI.

A standard curve was prepared using calibrators comprised of MHPG in artificial urine treated in the same fashion as the samples. The standard curve was stored in the instrument and samples were read off the curve.

The percentage of spiked MHPG recovered was determined as follows: Endogenous MHPG (0 mg/ml spike) was subtracted from the urine spike levels and divided by the target value of the MHPG spike.

Adjusted concentration =

Concentration measured − endogenous $MHPG$.

$$\% \text{ Recovery} = \frac{\text{Adjusted concentration}}{\text{Concentration of } MHPG \text{ spiked}} \times 100$$

The results are shown in the following table:

| Spike Concentration (n = 5) | % Recovery |
|---|---|
| 0.38 mg/mL | 104 |
| 0.75 mg/mL | 105 |
| 1.50 mg/mL | 104 |

| Spike Concentration (n = 5) | % Recovery |
|---|---|
| 3.00 mg/mL | 103 |

EXAMPLE XX

This example illustrates the function of magnesium silicate in the pretreatment of urine specimens. Both urine and glusulase contain fluorescent compounds that will interfere with the FPIA unless removed. The combination of 100-200 mesh magnesium silicate and 80% sodium chloride saturated 3M hydrochloric acid effectively reduces the background fluorescence.

16 replicates were prepared as follows: Phosphate buffer (pH 7+0.5), acetate buffer and enzyme were combined and incubated for 30 minutes at 56° C. The samples were divided into 4 groups of 4 each. Each group was treated with a different mesh size of magnesium silicate (16-30, 30-60, 60-100 and 100-200), followed by 80% sodium chloride-saturated hydrochloric acid. When a fixed volume of magnesium silicate is used, the finer the mesh the greater the decrease in sample fluorescence, as shown below.

| Mesh size | Background intensity (n = 4) |
|---|---|
| 16-30 | 2558 |
| 30-60 | 2203 |
| 60-100 | 1758 |
| 100-200 | 1046 |

EXAMPLE XXI

This example illustrates the stabilization of the MHPG-fluorescein tracer by an

The MHPG-fluorescein tracer was dissolved in various matrices and stored at 2-8 degrees C and 45 degrees C for 1 week. The stability of the tracer preparations was assessed on the basis of changes in the millipolarization after 45 degrees C heat stress. Results for 4 matrices are summarized below.

| Matrix | Polarization (2-8° C. baseline) | Polarization (45° C. stress) | Polarization change |
|---|---|---|---|
| #1 | 200.5 | 184.1 | 16.4 |
| #2 | 222.2 | 147.3 | 74.9 |
| #3 | 207.9 | 188.1 | 19.8 |
| #4 | 206.1 | 175.8 | 30.3 |

All percentages are weight/volume unless otherwise noted.

1. 25% (v/v) dimethyl sulfoxide, 75% (v/v) ethylene glycol, 1% sodium chloride, 0.1% sodium azide, 0.1% sodium metabisulfite.
2. 0.5% sodium thiosulfate in 0.1M phosphate buffer, 0.1% sodium azide, 0.01% bovine gamma globulin.
3. 95% [45% (v/v) dimethyl sulfoxide in 1M sodium chloride] 5% ethylene glycol.
4. 25% (v/v) dimethyl sulfoxide, 25% (v/v) ethylene lycol, 50% (v/v) saline [0.9% (w/v) sodium chloride in water], 1% sodium thiosulfate, 0.1% sodium azide, 0.01% bovine gamma globulin, 0.1% ethylene diamine tetraacetate.

Matrix #1 clearly provides the most stability to the tracer as evidenced by the relatively small drop in polarization over 7 days at 45 degrees C.

EXAMPLE XXII

This example illustrates the development of desirable antisera in multiple rabbits.

Figure 20:
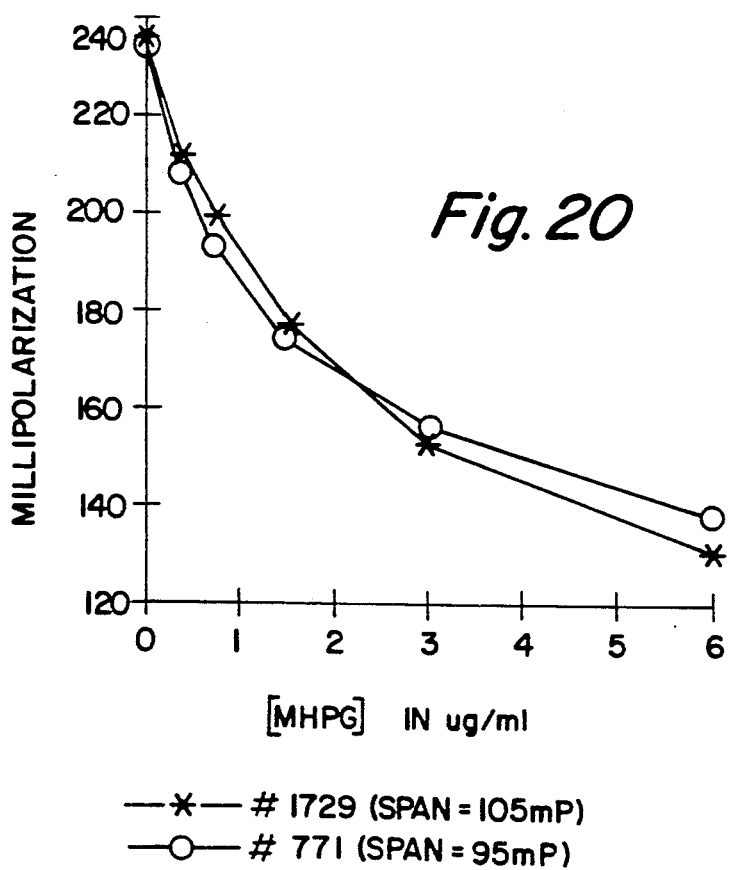
FIG. 20 shows representative standard curves found using antisera obtained from different animals.

Two rabbits were inoculated and boosted with the aforedescribed immunogen. Representative standard generated using antisera from each animal are shown in FIG. 20.

EXAMPLE XXIII

This example demonstrates the specificity of the MHPG antisera with regard to crossreactivity. The compounds listed below were dissolved in phosphate buffer and diluted to the following levels: 0.001, 0.01, 0.1, and 1.0 micrograms/ml. Each solution was hydrolyzed, extracted and tested as a sample. Percent crossreactivity was determined as follows:

$$\% \text{ Crossreactivity} = \frac{\text{Concentration measured}}{\text{Concentration of analyte spiked}} \times 100$$

Percent crossreactivity for all of the compounds at all four levels was less than 0.1%.

L-Dopa
D-Dopa
Dopamine
(−) Arterenol
Epinephrine
D,L-3,4-Dihydroxyphenylglycol
Normetanephrine
Vanillylmandelic acid
Homovanillic acid
D,L-3,4-Dihydroxymandelic acid
L-B-3,4-Dihydroxyphenylalanine methyl ester

What is claimed is:

1. A compound having the structure:

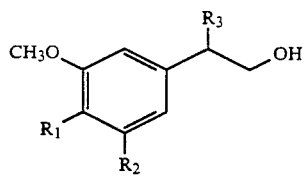

wherein $R_1$ is OH, $R_2$ is R—Z—Q wherein R is $CH_2CH=CH$, Z is CO and Q is bovine serum albumin or 4′-aminomethylfluorescein and $R_3$ is OH.

2. A process for determining the 3-methoxy-4-hydroxyphenylglycol content of a fluid sample, which comprises the steps of:

(a) contacting the fluid sample with one or more enzymes possessing sulfatase and glucuronidase activity;
   (b) contacting said fluid sample with a 3-methoxy-4-hydroxyphenylglycol antiserum produced by immunizing with an immunogen having the structure

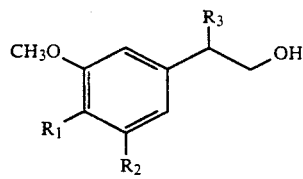

wherein
$R_1$ is OH, F, Br, Cl, I $OPO_3H$, $OSO_3H$, or

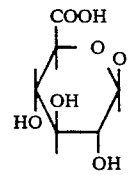

$R_2$ is R—Z—Q,
$R_3$ is H, OH, $CH_3$ or $C_2H_5$,
Q is a poly (amino acid) or a poly (amino acid) derivative or another immunologically active carrier,
Z, is N, NH, $SO_2$, $PO_2$, or PSO, and
R is a linking group having a total of from 0 to 20 carbon atoms and heteroatoms arranged in a straight or branched chain and containing up to two ring structures, and including up to 7 heteroatoms, and a metal silicate resin;

(c) removing the resin and retaining the supernatant;
   (d) contacting said supernatant with a compound of claim 1 capable of producing a detectable fluorescence polarization response to the presence of said 3-methoxy-4-hydroxyphenylglycol antiserum;
   (e) passing plane polarized light through the resulting solution from step (d) to obtain a fluorescence polarization response; and
   (f) detecting the fluorescence polarization response of the solution of step (e) as a measure of 3-methoxy-4-hydroxyphenylglycol content of the sample.

3. The process of claim 2 wherein the enzyme possessing sulfatase and glucuronidase activity is glusulase.

4. Antibodies to a compound having the structure:

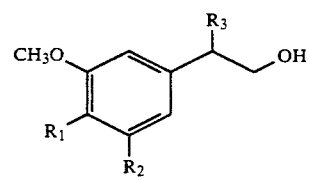

wherein:
$R_1$ OH, F, Br, Cl, I $OPO_3H$, $OSO_3H$, or

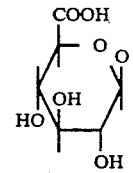

$R_2$ is R—Z—Q;
$R_3$ is H, OH, $CH_3$ or $C_2H_5$;
Q is a poly or a poly (amino acid) derivative or another immunologically active carrier;
Z is N, NH, $SO_2$, $PO_2$, or PSO; and
R is a linking group having a total of from 0 to 20 carbon atoms and heteroatoms arranged in a straight or branched chain and containing up to two ring structures, and including up to 7 heteroatoms.

* * * * *

UNITED STATES PATENT AND TRADEMARK OFFICE
CERTIFICATE OF CORRECTION

PATENT NO. : 5,145,791
DATED : September 8, 1992
INVENTOR(S) : Zeitvogel et al.

It is certified that error appears in the above-identified patent and that said Letters Patent is hereby corrected as shown below:

Column 22, line 50, after "$R_1$" insert --is--.

Signed and Sealed this

Twenty-second Day of December, 1992

Attest:

DOUGLAS B. COMER

Attesting Officer        Acting Commissioner of Patents and Trademarks